United States Patent
Shener-Irmakoglu et al.

(10) Patent No.: US 9,546,662 B2
(45) Date of Patent: *Jan. 17, 2017

(54) MEDICAL PUMP

(71) Applicant: SMITH & NEPHEW, INC., Memphis, TN (US)

(72) Inventors: Cemal Shener-Irmakoglu, Woburn, MA (US); Brian J. Loreth, Braintree, MA (US); Rafal Z. Jezierski, Middleton, MA (US); Paul Robert Duhamel, Groton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 904 days.

This patent is subject to a terminal disclaimer.

(21) Appl. No.: 13/682,220

(22) Filed: Nov. 20, 2012

(65) Prior Publication Data

US 2014/0140815 A1   May 22, 2014

(51) Int. Cl.
| | |
|---|---|
| *A61M 1/00* | (2006.01) |
| *A61M 3/02* | (2006.01) |
| *A61B 17/32* | (2006.01) |
| *F04D 13/02* | (2006.01) |

(Continued)

(52) U.S. Cl.
CPC ......... *F04D 13/02* (2013.01); *A61B 17/32002* (2013.01); *A61M 1/0064* (2013.01); *A61M 1/0066* (2013.01); *A61M 3/0258* (2013.01); *A61B 2017/00553* (2013.01);

(Continued)

(58) Field of Classification Search
CPC .... F04D 13/02; A61M 3/0258; A61M 1/0066; A61M 1/0064; A61B 17/32002; A61B 2017/00553; A61B 2217/005; A61B 2217/007

See application file for complete search history.

(56) References Cited

U.S. PATENT DOCUMENTS

| | | | |
|---|---|---|---|
| 5,176,629 | A | 1/1993 | Kullas et al. |
| 5,569,275 | A | 10/1996 | Kotula et al. |
| 5,685,821 | A | 11/1997 | Pike |

(Continued)

FOREIGN PATENT DOCUMENTS

CA       2000621 A1      4/1990

OTHER PUBLICATIONS

International Search Report from corresponding PCT application No. PCT/US2013/070558, mailed Mar. 4, 2014, total pp. 5.

*Primary Examiner* — Richard Edgar
*Assistant Examiner* — Brian P Wolcott

(57) ABSTRACT

A surgical instrument includes a hub, a rotating member, an impeller, and an impeller enclosure. The hub has a proximal portion and a distal portion and defines a lumen therebetween. The distal portion of the hub includes a sleeve portion configured to rotatably support the rotating member. The rotating member extends through the hub and has a proximal end and a distal end. The proximal end of the rotating member is configured to couple to an external driving mechanism. The impeller is coupled to the distal end of the rotating member and is configured to accelerate fluid flowing into or out of the lumen. The impeller enclosure is coupled to the distal portion of the hub and defines an impeller volume around the impeller. One or more openings are defined around the sleeve portion of the hub such that the lumen is in fluid communication with the impeller volume.

22 Claims, 10 Drawing Sheets

(51) Int. Cl.
*A61B 17/00* (2006.01)
*A61B 17/3207* (2006.01)

(52) U.S. Cl.
CPC .......... *A61B 2017/320775* (2013.01); *A61B 2217/005* (2013.01); *A61B 2217/007* (2013.01)

(56) References Cited

U.S. PATENT DOCUMENTS

| | | | |
|---|---|---|---|
| 5,709,698 | A | 1/1998 | Adams et al. |
| 5,746,721 | A | 5/1998 | Pasch et al. |
| 5,792,167 | A | 8/1998 | Kablik et al. |
| 5,800,383 | A | 9/1998 | Chandler et al. |
| 6,129,698 | A | 10/2000 | Beck |
| 6,451,017 | B1 | 9/2002 | Moutafis et al. |
| 7,344,546 | B2 * | 3/2008 | Wulfman ............... A61B 5/061 606/159 |
| 2003/0093103 | A1 | 5/2003 | Malackowski et al. |
| 2003/0108429 | A1 | 6/2003 | Angelini et al. |
| 2004/0204679 | A1 | 10/2004 | Visconti et al. |
| 2007/0010823 | A1 | 1/2007 | Kucklick |
| 2007/0161978 | A1 | 7/2007 | Fedenia et al. |
| 2007/0233003 | A1 | 10/2007 | Radgowski et al. |
| 2008/0033349 | A1 | 2/2008 | Suzuki |
| 2008/0154185 | A1 | 6/2008 | Blight |
| 2010/0268236 | A1 | 10/2010 | Moutafis et al. |
| 2011/0224600 | A1 | 9/2011 | Orlandi |

* cited by examiner

MEDICAL PUMP

TECHNICAL FIELD

This document relates to a medical pump.

BACKGROUND

Various types of medical pump systems are used in endoscopy, and particularly in arthroscopy. Some pump systems may use a dedicated electric powered control unit that generates fluid flow within a tubeset. In some cases, a non-powered pumping system may be used. A gravity-fed tubeset, which establishes fluid flow via gravity alone by raising a fluid bag above a surgical site, is one such example. Alternatively, or additionally, fluid from the fluid bag may be forced to the surgical site by squeezing the fluid bag and thus increasing fluid pressure. In some cases, an inline flexible fluid chamber may be squeezed manually or by a mechanical device to augment gravity flow by providing additional flow/pressure.

SUMMARY

According to one aspect, a surgical instrument includes a hub, a rotating member, an impeller, and an impeller enclosure. The hub has a proximal portion and a distal portion and defines a lumen between the proximal and distal portions. The distal portion of the hub includes a sleeve portion configured to rotatably support the rotating member. The rotating member extends through the hub and has a proximal end and a distal end. The proximal end of the rotating member is configured to couple to an external driving mechanism. The impeller is coupled to the distal end of the rotating member and is configured to accelerate fluid flowing into or out of the lumen. The impeller enclosure is coupled to the distal portion of the hub and defines an impeller volume around the impeller. One or more openings are defined around the sleeve portion of the hub such that the lumen is in fluid communication with the impeller volume.

Implementations of this aspect may include one or more of the following features. For example, the impeller may be an axial impeller configured to accelerate fluid in a direction substantially parallel to an axis of rotation of the rotating member. The impeller may be a centrifugal impeller configured to accelerate fluid in a direction substantially perpendicular to an axis of rotation of the rotating member. A design of the impeller may be associated with a particular pump type, the particular pump type being selected from the group consisting of a centrifugal pump, a gear pump, a screw pump, a vane pump, a lobe pump, and a peristaltic pump. The impeller enclosure may be integrated with the hub. The surgical instrument may be configured to be used in irrigation such that fluid flowing out of the lumen of the hub is accelerated by the impeller. The surgical instrument may be configured to be used in aspiration such that fluid the impeller accelerates fluid flowing into the lumen of the hub. The surgical instrument may further include a shaver handpiece. The shaver handpiece may include the external driving mechanism. The surgical instrument may further include a fluid bag, wherein the fluid bag is in fluidic communication with the lumen of the hub. The surgical instrument may further include a control unit configured to control an RPM of the external driving mechanism.

According to another aspect, a surgical instrument system includes a shaver handpiece and a pump cartridge configured to pump fluid. The shaver handpiece includes a drive mechanism. The drive mechanism includes a distal end configured to releasably couple to a proximal end of a rotary cutter. The pump cartridge includes a hub configured to releasably couple to the shaver handpiece, a rotating member rotatably supported by the hub and configured to couple to the distal end of the shaver handpiece drive mechanism, and an impeller coupled to the rotating member and configured to accelerate fluid.

Implementations of this aspect may include one or more of the following features. For example, the hub of the pump cartridge may further define a lumen configured to allow the fluid to flow therethrough. The shaver handpiece may further define a lumen configured to be in fluidic communication with the lumen of the pump cartridge. The surgical instrument system may further include a fluid reservoir in fluid communication with the pump cartridge. The surgical instrument system may further include a control unit configured to control an RPM of the external driving mechanism. The drive mechanism may be driven in a first direction to pump fluid toward a surgical site. The drive mechanism may be driven in a second direction opposite the first direction to pump fluid away from the surgical site.

According to another aspect, a surgical instrument includes a hub having a proximal portion and a distal portion that is configured to rotatably support a rotating member, a rotating member extending through the hub, an impeller enclosure coupled to the distal portion of the hub and defining an impeller volume around an impeller, and an impeller coupled to the distal end of the rotating member and configured to accelerate fluid flowing into or out of the impeller volume. The rotating member has a proximal end and a distal end, and the proximal end is configured to couple to an external driving mechanism;

Implementations of this aspect may include one or more of the following features. For example, the impeller enclosure may define an inlet and an outlet through which fluid enters and exits the impeller volume, respectively. The impeller may be a centrifugal impeller configured to accelerate fluid in a direction substantially perpendicular to an axis of rotation of the rotating member.

The details of one or more implementations are set forth in the accompanying drawings and the description below. Other features, aspects, and advantages will become apparent from the description, the drawings, and the claims.

DETAILED DESCRIPTION

A pump cartridge may be used for pumping fluid. The pump cartridge may, for example, be used for joint/organ distension and irrigation and/or for tissue resection and evacuation. The pump cartridge may be configured to couple to an existing shaver handpiece, which provides the motor unit.

Figure 1:
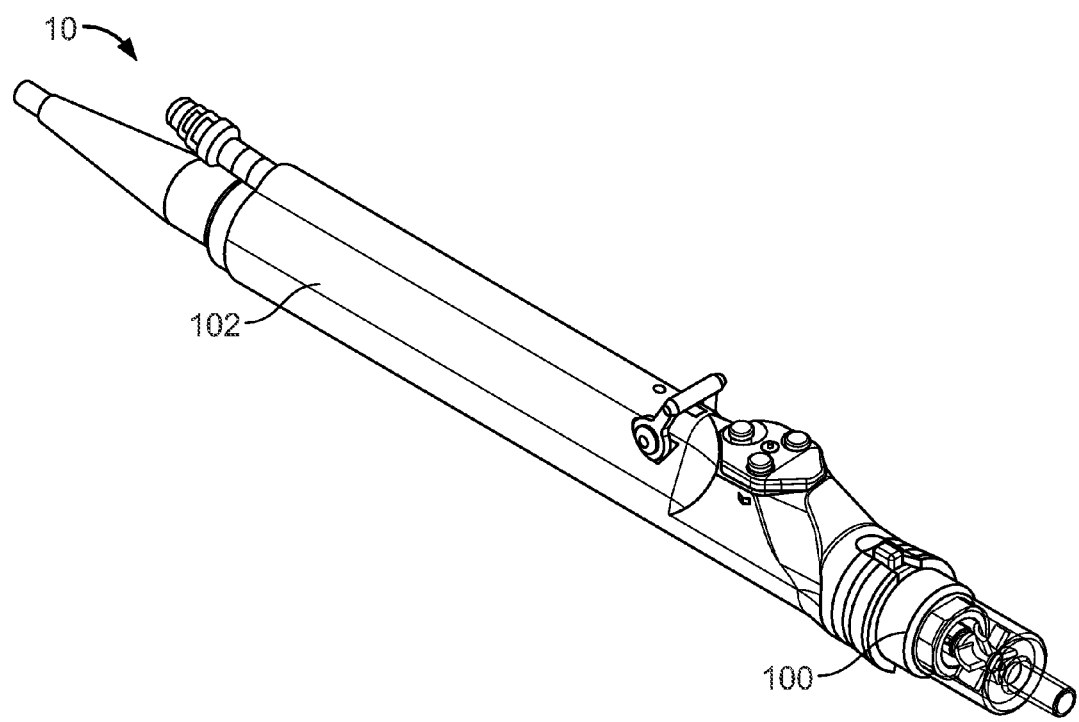
FIG. 1 is a perspective view of a pump cartridge coupled to a handpiece that may also be used with, for example, a rotary cutter attachment.

Referring to FIG. 1, a pumping system 10 can include a pump cartridge 100 and a shaver handpiece 102. The pump cartridge 100 can releasably couple to the shaver handpiece 102 by, for example, being inserted and latched within a distal bore (not shown) of the shaver handpiece 102. Various types of shaver handpieces, motor drive units, or other similar surgical instruments may be used in conjunction with the pump cartridge 100; further descriptions of such handpieces may be found in U.S. Pat. Nos. 5,871,493 and 7,766,844, which are both incorporated herein by reference in their entirety.

Figure 2A:
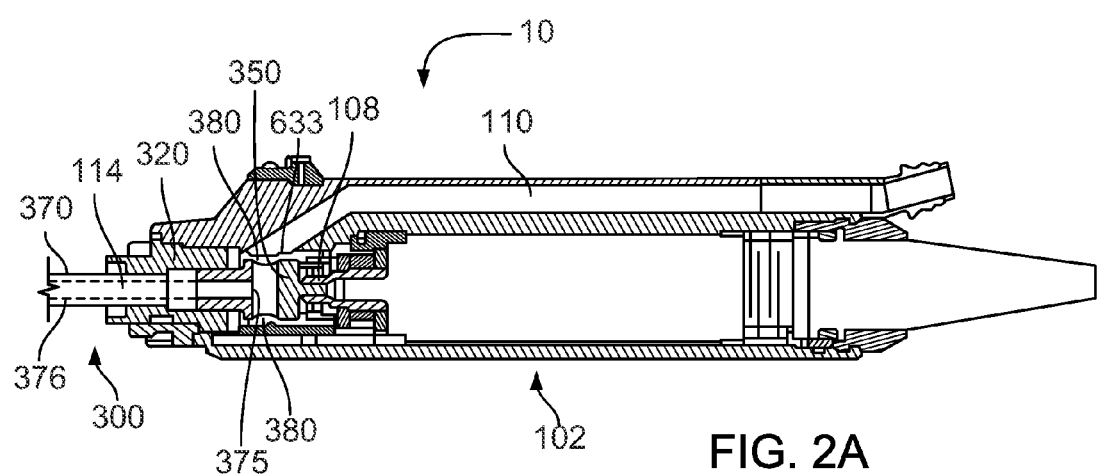
FIG. 2A is a side cross-sectional view of a rotary cutter attachment coupled to the handpiece.
Figure 2B:
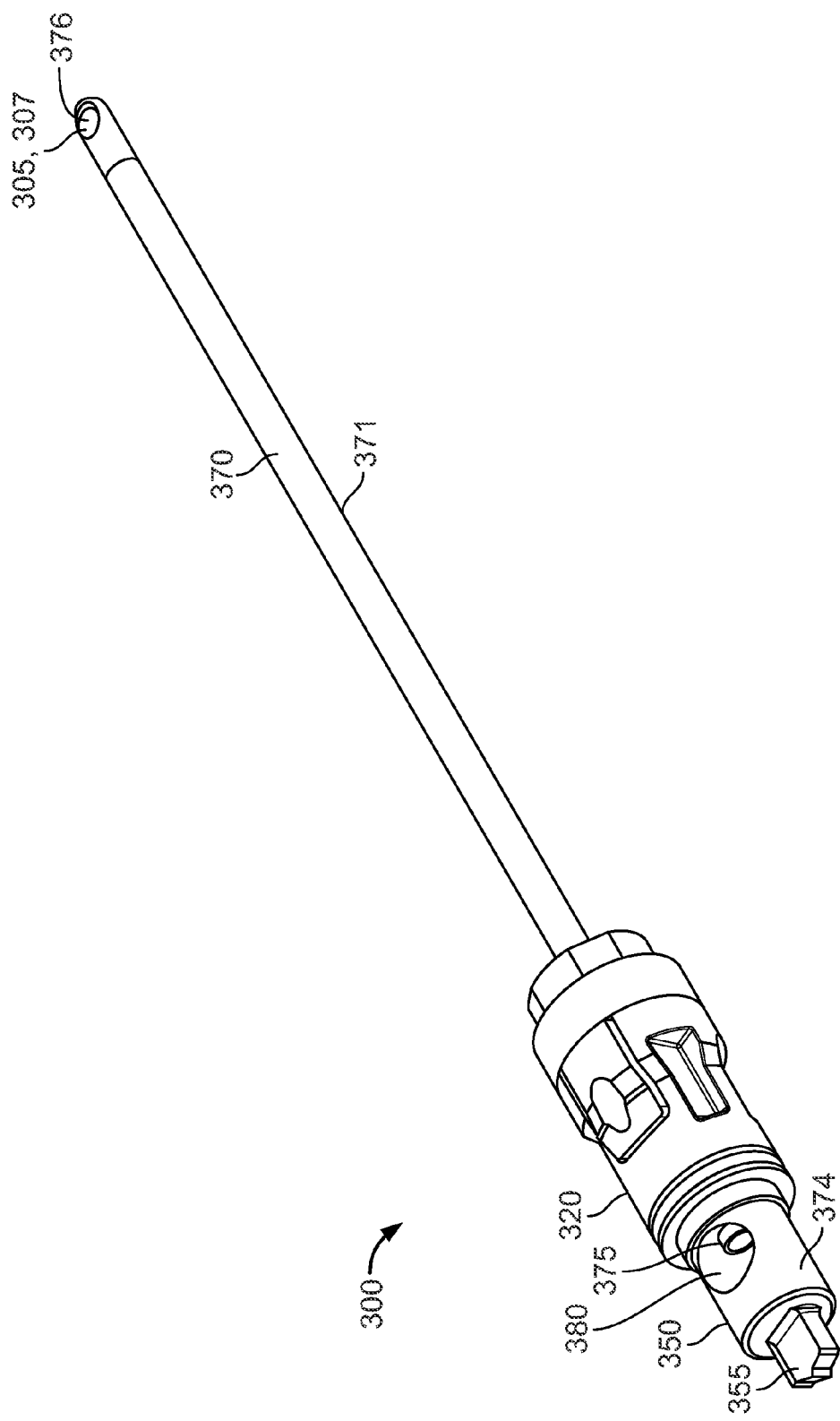
FIG. 2B is a perspective view of the rotary cutter attachment.

Referring to FIGS. 2A and 2B, the shaver handpiece 102 is shown coupled to a rotary cutter attachment 300. The shaver handpiece 102 contains a drive mechanism 108, such as an electric motor, and further contains a fluid channel 110. The drive mechanism 108 can engage and impart rotational motion to the attachment 300, and the fluid channel 110 can be in fluidic communication with a lumen 114 defined within the attachment 300.

In some implementations, the rotary cutter attachment 300 shown in FIG. 2B can be used to resect tissue by using a tube-in-tube construction that shears tissue disposed between cutting edges of an outer non-rotating tube 370 and an inner rotating shaft 374. The outer tube 370 can be connected to a hub 320 at a proximal region 371 of the outer tube 370, and the inner shaft 374 can be rotatably received in the hub 320 and the outer tube 370. The inner shaft 374 can include a tube 376 located within the outer tube 370. The tube 376 can define a lumen 114 and connect to a motor coupling 350 located in a proximal region of the shaft 374 and partially received within the hub 320. The motor coupling 350 can include an extension 355 coupled to the drive mechanism 108 that rotates the shaft 374 relative to the hub 320 and the outer tube 370. In some cases, the rotary cutter attachment 300 may include other types of cutters at its distal end, for example a burr cutter.

Returning to FIG. 2A, the fluid channel 110 can terminate at an aspiration opening 633 in order to, for example, apply suction to the lumen 114 to remove fluid and cut tissue from a surgical site. The lumen 114 can be positioned within the tube 376 of the shaft 374 (FIG. 3) and have a proximal opening 375 that communicates with a through hole 380 in the motor coupling 350. Suction may be applied through the fluid channel 110 to draw material through a side-facing window 305 in the outer tube 370 and a side-facing window 307 in the inner tube 376, into the lumen 114, and through the lumen opening 375 and both ends of the hole 380 to the fluid channel 110.

Figure 3A:
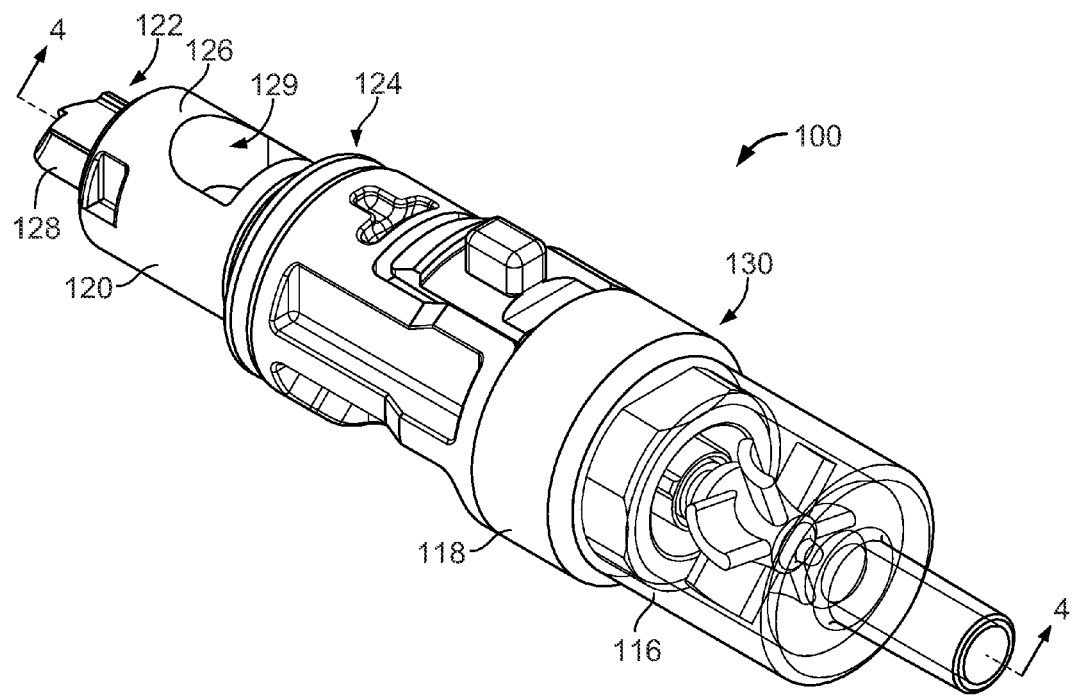
FIGS. 3A and 3B are perspective views of the pump cartridge, shown with and without an impeller enclosure, respectively.
Figure 3B:
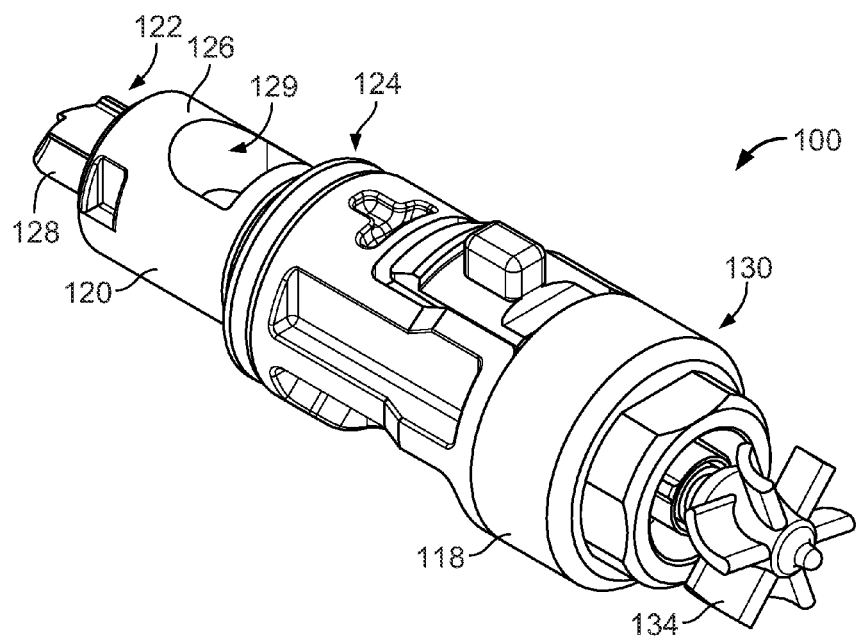

Referring now to FIGS. 3A and 3B, the pump cartridge 100 includes a stationary hub 118 and an inner rotating member 120. As mentioned, the pump cartridge 100 can be configured to couple to an existing handpiece, for example, the shaver handpiece 102. The inner rotating member 120 generally extends longitudinally through all or a portion of the hub 118 and is rotatably supported within the hub 118 as discussed further below. In some cases, a proximal end 122 of the rotating member 120 extends beyond a proximal portion 124 of the hub 118 and includes a motor coupling portion 126 for coupling to the drive mechanism. An extension 128, which can extend proximally from the motor coupling portion 126, can engage the drive mechanism 108, such that the rotational motion of the drive mechanism 108 can be transferred to the rotating member 120. An impeller enclosure 116, which is shown in FIG. 3A and removed for clarity in FIG. 3B, can be attached to a distal portion 130 of the hub 118. The impeller enclosure 116 may be removed, for example, during assembly or service of the pump cartridge 100. Alternatively, the impeller enclosure 116 can be integrally formed as a part of the pump cartridge 100, for example, as an extension of the hub 118.

Figure 4:
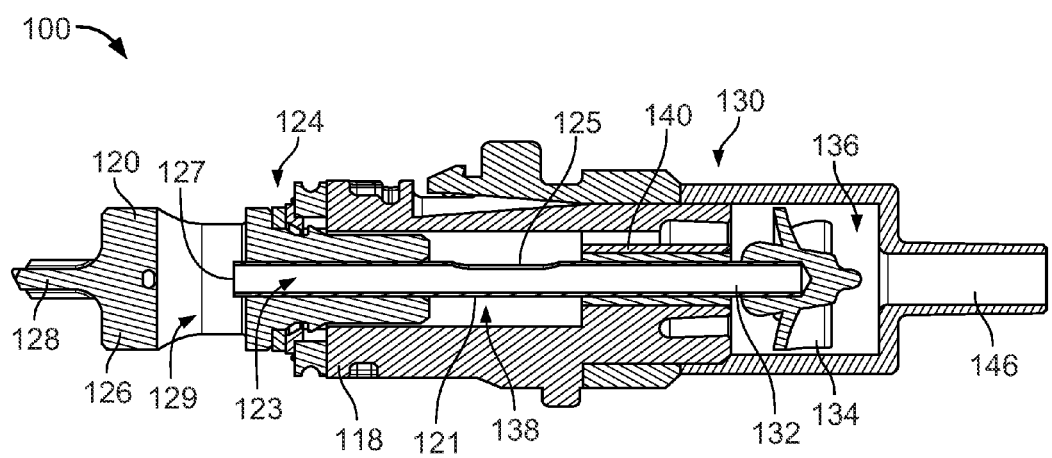
FIG. 4 is a side cross-sectional view of the pump cartridge.

Referring also to FIG. 4, the inner rotating member 120 can include a motor coupling portion 126 and a shaft portion 121 that is attached distally to the motor coupling portion 126. A distal end 132 of the shaft portion 121 can extend beyond the distal portion 130 of the hub 118, and an impeller 134 can be attached to the distal end 132. The impeller enclosure 116 surrounds the impeller 134 and defines an impeller volume 136 around the impeller 134. When the motor coupling portion 126 is coupled to the drive mechanism 108, a rotation of the drive mechanism 108 will result in a corresponding rotation of the impeller 134, which in return, as discussed further below, will result in the pumping of fluid. The impeller 134 can be an axial impeller that is designed to accelerate fluid in a direction substantially parallel to the impeller's axis of rotation.

The pump cartridge 100 as illustrated in FIG. 4 further defines a lumen 138 that generally extends between the proximal end 124 and the distal end 130. In some cases, a proximal end of the lumen 138 may be partially or fully blocked by a portion of the motor coupling unit 126. As such, in order to establish a flow path between a fluid-carrying lumen of the shaver handpiece, such as the fluid channel 110 of the shaver handpiece 102, and the impeller volume 136, an additional fluid path may be established through the rotating member 120. For example, the shaft portion 121 may define a lumen 123 that is in fluid communication with the lumen 138 via a body opening 125. Additionally, a proximal end of the shaft portion 121 may include an opening 127 that is in fluid communication with a through hole 129 defined within the motor coupling portion 126, wherein the through hole 129 can be in fluid communication with the fluid-carrying lumen of the handpiece, for example, the fluid channel 110. The fluid-carrying lumen of the shaver handpiece can further be in fluid communication with a fluid reservoir, for example a fluid bag 150 (see FIG. 6), such that a fluid flow path is established between the fluid reservoir and the impeller volume 136. Alternatively, or additionally, the fluid reservoir may directly connect to and establish a fluid flow path with the pump cartridge 100 without going through the handpiece 102. During an irrigation procedure, as discussed further below, fluid exits the impeller volume 136 via an opening in the enclosure 116, for example a tube connection 146. Conversely, during an aspiration procedure, fluid enters the impeller volume 136 via, for example, the tube connection 146.

The inner rotating member 120 can be rotatably supported within the pump cartridge 100. For example, as shown in FIG. 4, the distal end 132 of the shaft portion 121 can be supported by a sleeve portion 140 of the hub 118, wherein the sleeve portion 140 sealingly surrounds a circumference of the shaft portion 121 of the rotating member 120 to allow it to rotate about a longitudinal axis of hub 118. The interface between an inner surface of the sleeve portion 140 and a circumference of the rotating member 120 can further include various seals, bushings, bearings, and the like to help reduce friction between the two surfaces while also preventing, in some cases, the unwanted passage of fluid therebetween.

Figure 5:
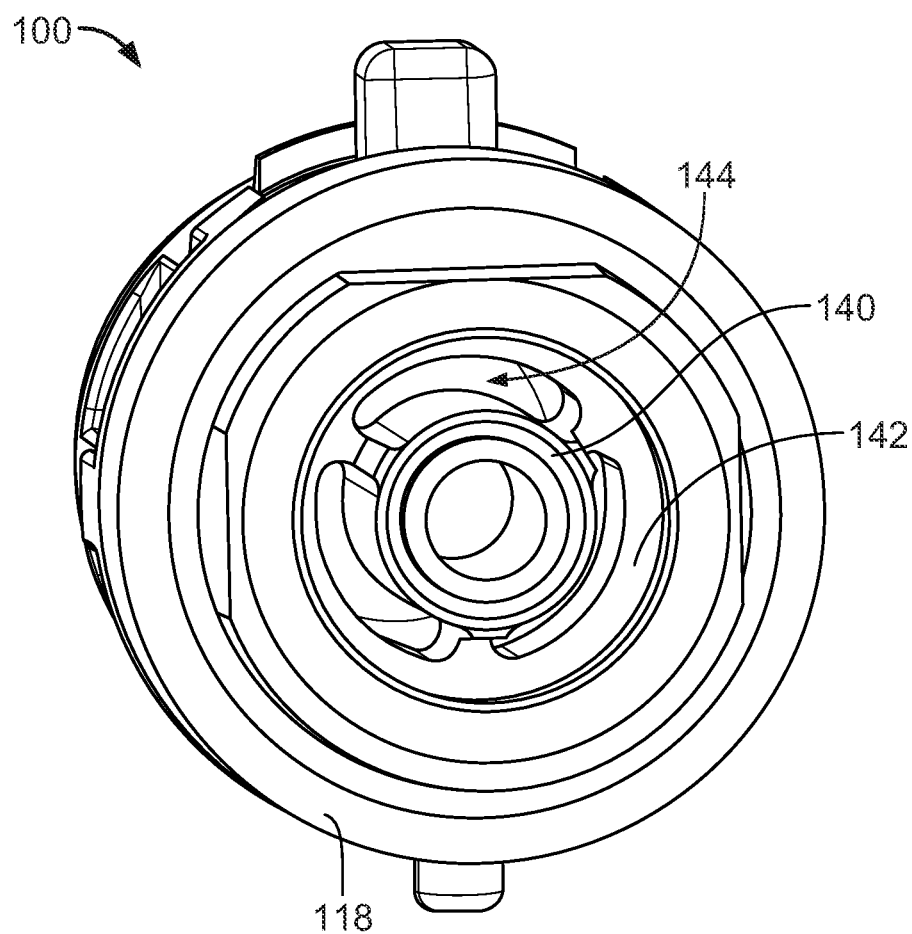
FIG. 5 is a front perspective view of a portion of the pump cartridge.

Referring also to FIG. 5, a distal end of the lumen 138 can be defined by an end face 142 of the hub 118, and the sleeve portion 140 can be an integrated or a separately attached part of the end face 142. The end face 142 generally provides a separation between fluid within the lumen 138 and fluid within the impeller volume 136. In order to provide fluidic communication between the lumen 138 and the impeller volume 136, the end face 142 can define one or more fluid openings 144. As shown in FIG. 5, three fluid openings 144 are defined in the end face 142 and equally spaced about the rotating member 120 (FIG. 4). Alternative fluid opening configurations in or near the end face 142 are also possible. In some cases, one or more fluid openings may be defined through the rotating member 120 and/or the impeller 134.

Figure 6:
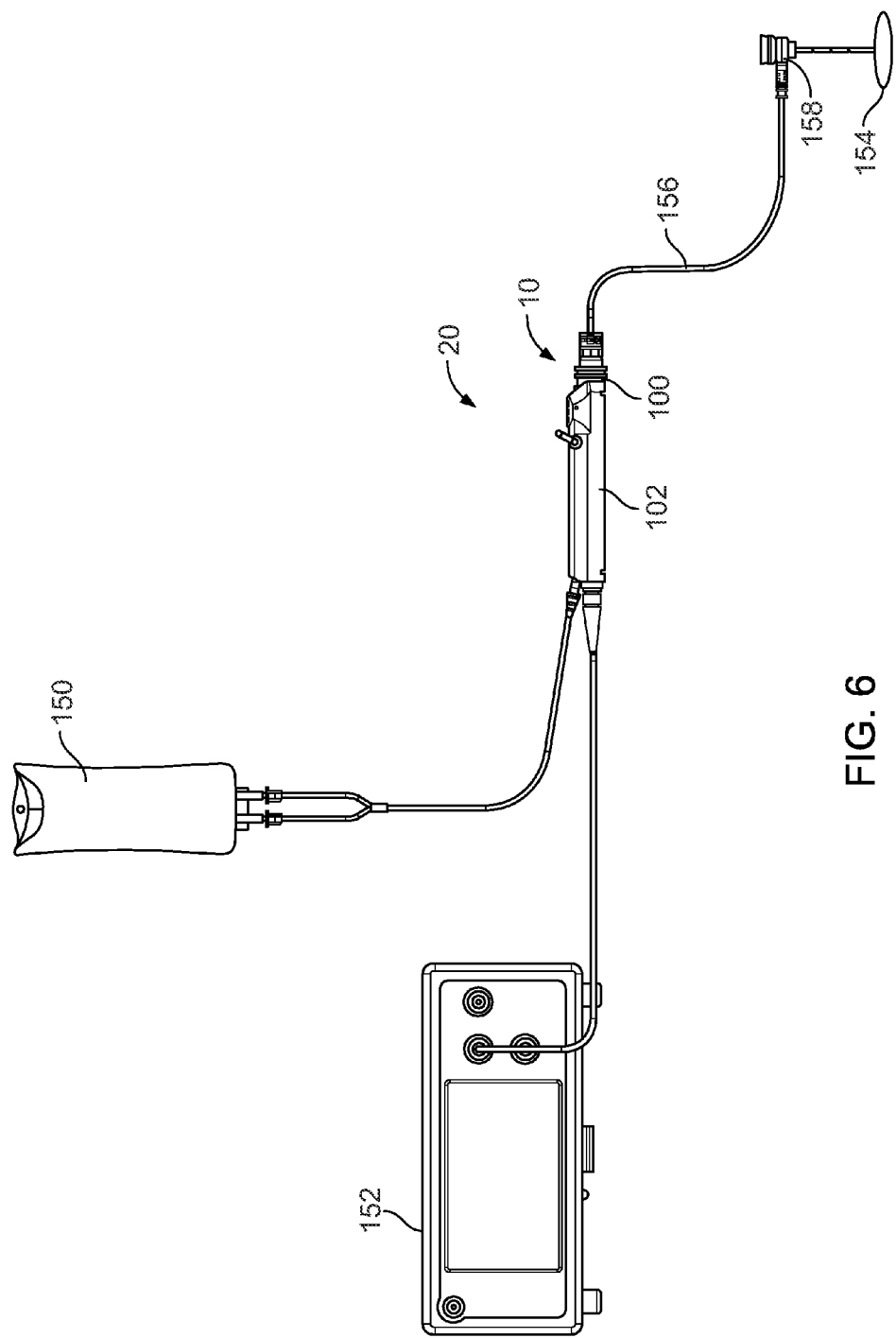
FIG. 6 illustrates an example pumping and control system that includes the pump cartridge.

An example of a complete pumping and control system 20 is shown in FIG. 6. As shown, the pumping system 10, as described above, is further connected to a fluid bag 150 and a control unit 152. The handpiece 102 and the control unit 152 may be part of an existing surgical shaving system, and the control unit 152 may be configured to electronically control the parameters of the rotary cutter that would be attached to the handpiece 102. When the handpiece 102 is used with the rotary cutter attachment (not shown) or other non-pumping attachments, fluid flow from the fluid bag 150 to the surgical site 154 may be established by gravity through an alternative tubing line (not shown) that defines a fluid path between the fluid bag 150 and the surgical site 154.

Referring also to FIG. 4, when the pumping and control system 20 is connected to the pump cartridge 100, fluid may be pumped to the surgical site 154, for example to provide irrigation, by rotating the impeller 134 in a first direction (e.g. clockwise) such that fluid in the impeller volume 136 is accelerated toward the surgical site 154. In this instance, fluid from a fluid reservoir, such as the fluid bag 150, flows through the lumen 138, passes through the fluid openings 144, and enters the impeller volume 136, where it is accelerated out of the tube connection 146. As shown in FIG. 6, the tube connection 146 can further be connected to a tubing 156. The tubing 156 can in turn be connected to a cannula 158 that can be placed in or near the surgical site 154.

Similarly, when the pumping and control system 20 is connected to the pump cartridge 100, fluid may be pumped away from the surgical site 154, for example to provide aspiration, by rotating the impeller 134 in a second direction that is opposite the first direction (e.g. counterclockwise). In this case, fluid in the impeller volume 136 is accelerated toward the lumen 138 such that fluid is pumped from the surgical site 154 toward, for example, a waste container (not shown) that is fluidically connected to the handpiece 102.

In order to control the impeller rotation as described above for both irrigation and aspiration procedures, as well as in other procedures where pumping fluid toward/from the surgical site is desired, the control unit 152 can provide necessary electrical power/signals to the drive mechanism 108 in the shaver handpiece 102 (FIG. 2A). For example, the control unit 152 can be set to drive/rotate the drive mechanism, and consequently the impeller 134 coupled thereto, to rotate at 5000 RPM. Impeller rotation of 5000 RPM may correspond to, for example, a pump pressure of approximately 200~250 mm Hg and a flow rate of 2~2.5 L/min. However, the relationship between impeller rotation, pump pressure, and/or flow rate typically depend on a multitude of factors including, but not limited to, shape of the impeller 134 and the enclosure 116 as well as the characteristics of the fluid being pumped. As such, a calibration chart/plot may be generated to establish a general or fluid-specific relationship between rotation speed provided by the control unit 152 and resulting fluid pumping characteristics. In some cases, the impeller may rotate between 0 and 5000 RPM. In some cases, the impeller may rotate at speeds up to 15,000 RPM. In some cases, the impeller may rotate at speeds up to and beyond 20,000 RPM.

Figure 7:
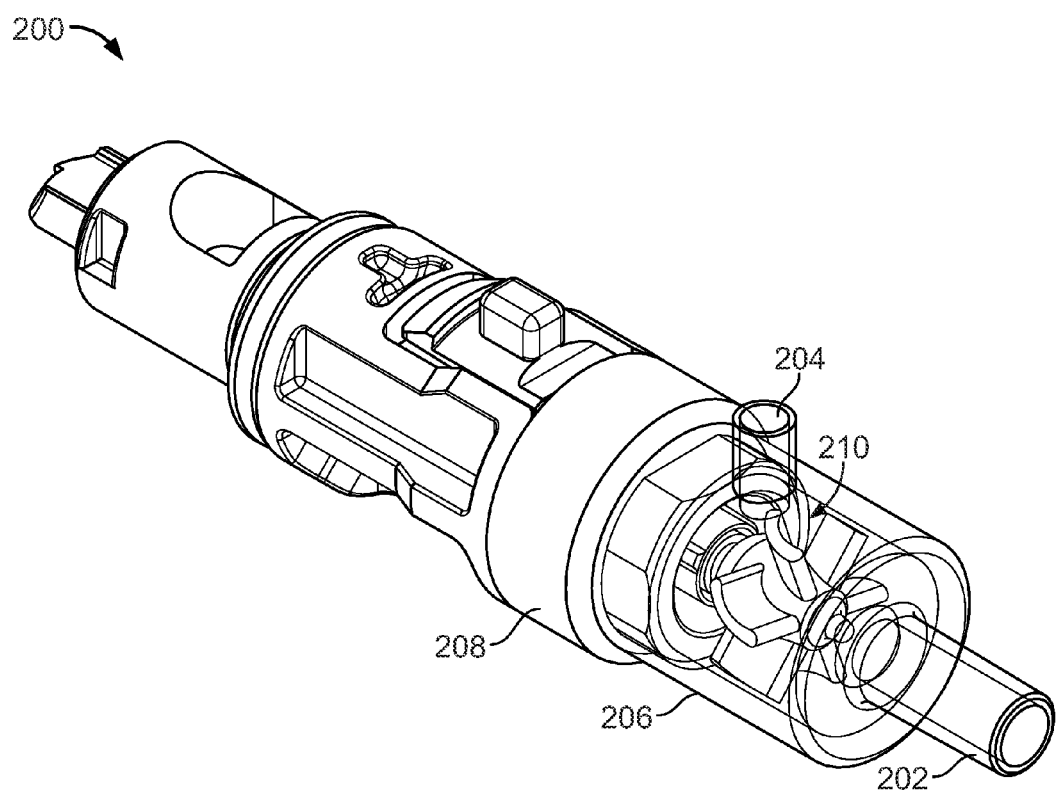
FIG. 7 is a perspective view of an alternative implementation of the pump cartridge

Referring to FIG. 7, in an alternative implementation, a pump cartridge 200 may establish a fluidic connection between a tube connection 202 and either a fluid reservoir (e.g. during irrigation) or a waste container (e.g. during aspiration) via a bypass opening 204 without going through a portion of the shaver handpiece 102 such as the fluid channel 110 (FIG. 2). The bypass opening 204 may be, for example, positioned on an outer wall of an enclosure 206 and oriented perpendicularly relative to the tube connection 202 as illustrated in FIG. 7. In some cases, the bypass opening 204 may be positioned at other portions of the pump cartridge 200, for example at a hub portion 208. When the fluid reservoir or the waste container establishes a direct fluidic connection with an impeller volume 210 defined by the enclosure 206, for example via the bypass opening 204 positioned on the enclosure 206, the impeller volume 210 may not be in fluid communication with other portions of the pump cartridge 200. In some cases, the pump cartridge 200 may not include a fluid carrying lumen.

Figure 8:
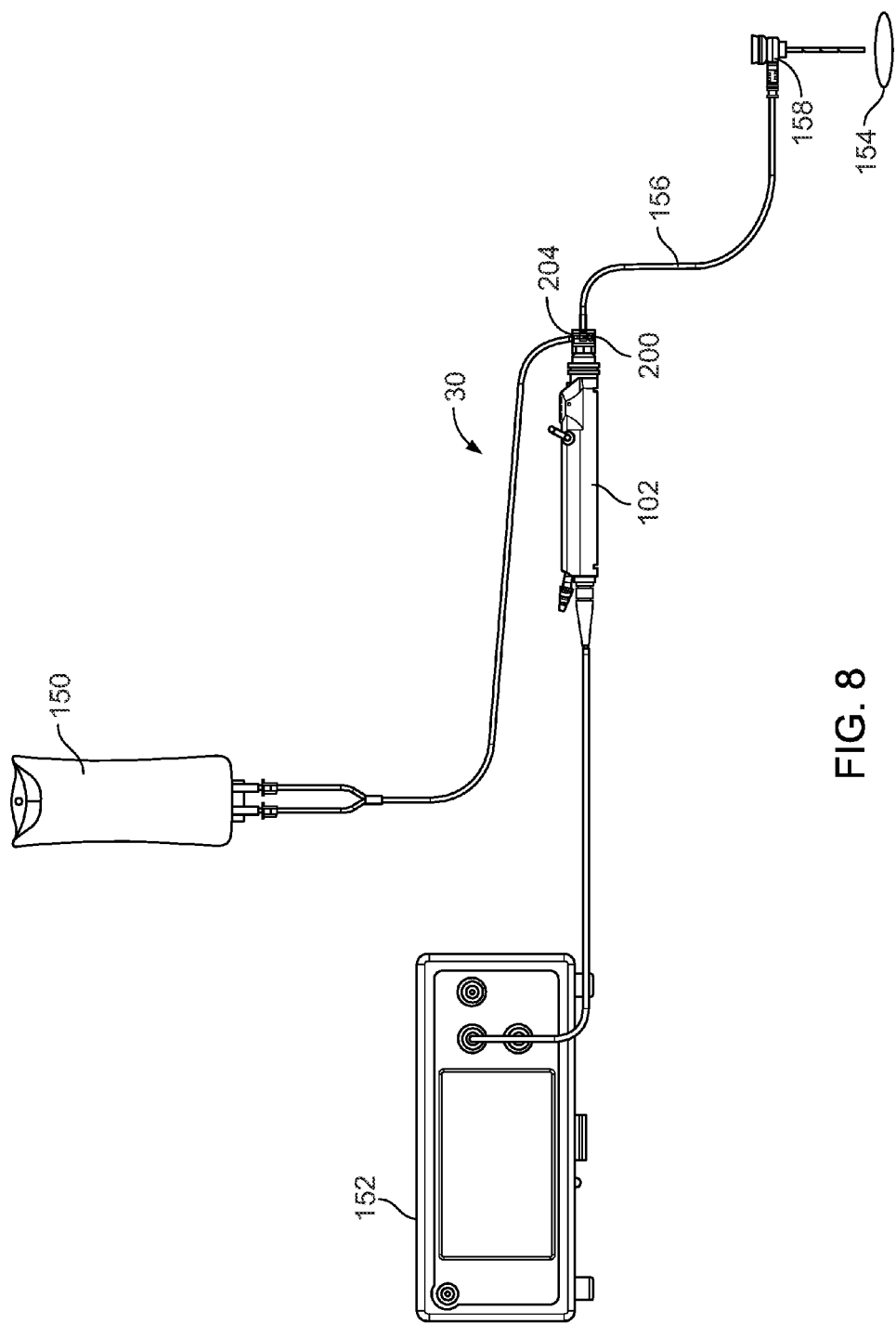
FIG. 8 illustrates an example pumping and control system that includes the alternative implementation of the pump cartridge.

Referring also to FIG. 8, a pumping system 30 having the pump cartridge 200 is shown further connected to the fluid bag 150 and the control unit 152. As shown in the figure, a fluid path is established between the fluid bag 150 and the surgical site 154 without going through the handpiece 102.

Figure 9A:
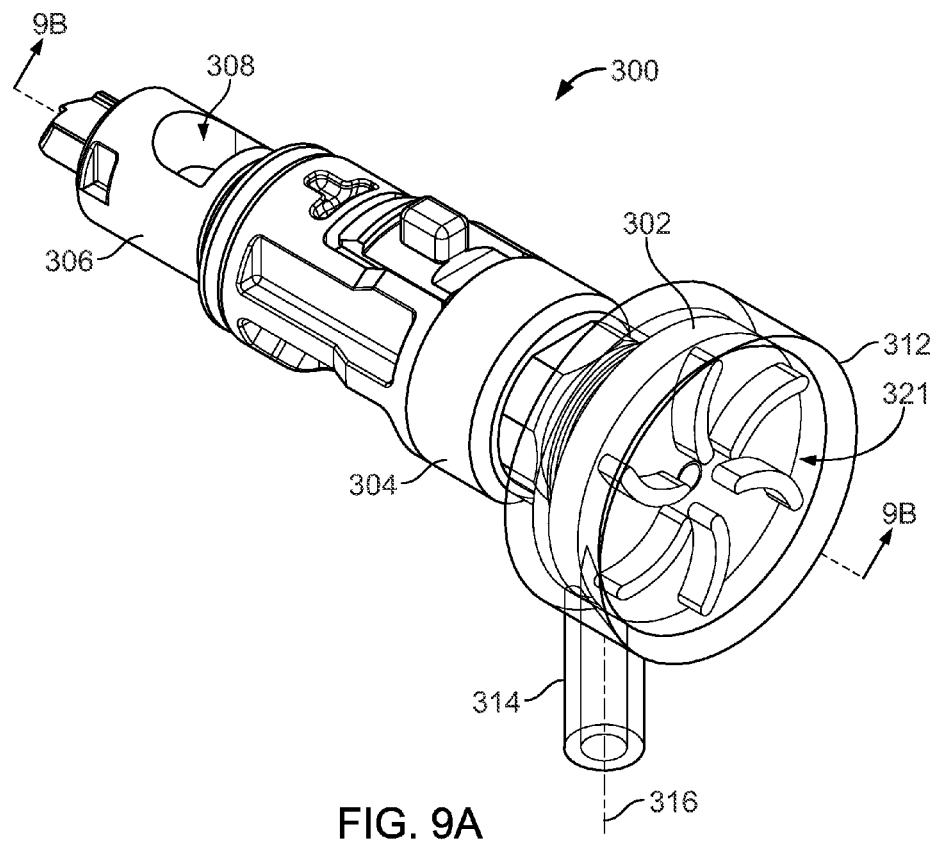
FIGS. 9A and 9B are perspective and side cross-sectional views, respectively, of another alternative implementation of the pump cartridge.
Figure 9B:
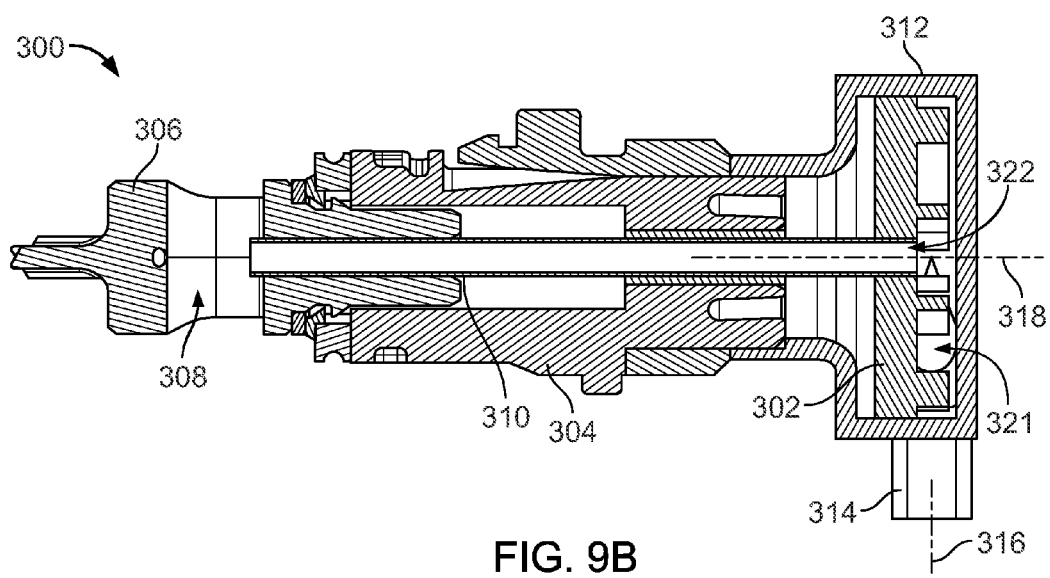

Alternative implementations of the pump cartridge 100, 200, may use an impeller that is designed to accelerate fluid at an angle relative to an axis of the rotating member 120. For example, referring to pump cartridge 300 as illustrated in FIGS. 9A and 9B, a centrifugal impeller 302 is rotatably coupled to a stationary hub 304. The pump cartridge 300 can include a rotating member 306 that extends through the pump hub 304 and that is configured to couple to an external drive mechanism. The rotating member 306 rotates about an axis of rotation 318. A proximal end of the rotating member 306 can define a through hole 308 that is in fluid communication with, for example, the fluid channel 110 of the handpiece 102 (FIG. 2A). The rotating member 306 can further include a hollow shaft 310 whose distal end is attached to the centrifugal impeller 302. An impeller enclosure 312 surrounds the impeller 302 and defines an impeller volume 321 around the impeller 302. The impeller enclosure 312 can include a tube connection 314 that extends away from the impeller volume 321 along an axis 316.

In use, for example during an irrigation procedure, fluid entering the cartridge 300 through the through hole 308 can flow within the hollow shaft 310 along the axis 318 and into the impeller volume 321 via an impeller opening 322. The fluid is subsequently pumped out of the impeller volume 321 along the axis 316 via the tube connection 314. As can be seen from the side view of the cartridge 300 in FIG. 9B, the centrifugal impeller 302 can accelerate fluid out of the tube connection 314 in a direction substantially perpendicular to the axis of rotation 318.

Other alternative implementations of the pump cartridge 100, 200, 300 may use an impeller that is a rotating, fluid-moving member associated with various rotary positive displacement-type pumps. In some cases, the rotary pump may comprise a gear pump having two meshed gears that rotate within an enclosure fitted around a periphery of the gear rotation range, wherein fluid is trapped and transferred between gear teeth and a wall of the enclosure. In some cases, the rotary pump may comprise a screw pump having two, opposing thread, counter-rotating screws that are mounted within the enclosure, wherein the rotation of the screws draws in fluid through the enclosure. In some cases, the rotary pump may comprise a vane pump having a rotor equipped with fixed or movable vanes that are offset within the enclosure, wherein the rotation of the rotor assembly results in deflection or sliding action of vanes to create variable volume fluid pockets that force the fluid through the enclosure. In some cases, the rotary pump may comprise a lobe, or roots type, pump having meshed, rotating helical lobes that trap and transfer fluid through the enclosure. In some cases, the rotary pump may comprise a peristaltic pump in which fluid contained within a flexible tube is pushed through by an occlusion-restitution cycle driven by a rotor equipped with a set of rollers located around the perimeter of the rotor.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

What is claimed is:

1. A surgical instrument comprising:
   a hub having a proximal portion and a distal portion, the hub defining a lumen between the proximal and distal portions, wherein the distal portion of the hub includes a sleeve portion configured to rotatably support a rotating member; the rotating member extending through the hub, the rotating member having a proximal end and a distal end, the proximal end of the rotating member being configured to couple to an external driving mechanism;
   an impeller coupled to the distal end of the rotating member and configured to accelerate fluid flowing into or out of the lumen; and
   an impeller enclosure coupled to the distal portion of the hub and defining an impeller volume around the impeller, wherein one or more openings are defined around the sleeve portion of the hub such that the lumen is in fluid communication with the impeller volume.

2. The surgical instrument of claim 1, wherein the impeller is an axial impeller configured to accelerate fluid in a direction substantially parallel to an axis of rotation of the rotating member.

3. The surgical instrument of claim 1, wherein the impeller is a centrifugal impeller configured to accelerate fluid in a direction substantially perpendicular to an axis of rotation of the rotating member.

4. The surgical instrument of claim 1, wherein a design of the impeller is associated with a particular pump type, the particular pump type being selected from the group consisting of a centrifugal pump, a gear pump, a screw pump, a vane pump, a lobe pump, and a peristaltic pump.

5. The surgical instrument of claim 1, wherein the impeller enclosure is integrated with the hub.

6. The surgical instrument of claim 1, wherein the surgical instrument is configured to be used in irrigation such that fluid flowing out of the lumen of the hub is accelerated by the impeller.

7. The surgical instrument of claim 1, wherein the surgical instrument is configured to be used in aspiration such that fluid the impeller accelerates fluid flowing into the lumen of the hub.

8. The surgical instrument of claim 1, further comprising a shaver handpiece, wherein the shaver handpiece comprises the external driving mechanism.

9. The surgical instrument of claim 1, further comprising a fluid bag, wherein the fluid bag is in fluidic communication with the lumen of the hub.

10. The surgical instrument of claim 1, further comprising a control unit configured to control an RPM of the external driving mechanism.

11. A surgical instrument system comprising:
   a shaver handpiece comprising a drive mechanism, the drive mechanism having a distal end configured to releasably couple to a proximal end of a rotary cutter; and
   a pump cartridge configured to pump fluid, the pump cartridge comprising: a hub configured to releasably couple to the shaver handpiece, a rotating member rotatably supported by the hub and configured to couple to the distal end of the shaver handpiece drive mechanism, and an impeller coupled to the rotating member and configured to accelerate fluid in an impeller volume, and an opening in the rotating member such that an interior of the rotary cutter is in fluid communication with the impeller volume.

12. The surgical instrument system of claim 11, wherein the hub of the pump cartridge further defines a lumen configured to allow the fluid to flow therethrough.

13. The surgical instrument system of claim 12, wherein the shaver handpiece further defines a lumen configured to be in fluidic communication with the lumen of the pump cartridge.

14. The surgical instrument system of claim 11, further comprising a fluid reservoir in fluid communication with the pump cartridge.

15. The surgical instrument system of claim 11, further comprising a control unit configured to control an RPM of the drive mechanism.

16. The surgical instrument system of claim 11, wherein the drive mechanism is driven in a first direction to pump fluid toward a surgical site.

17. The surgical instrument system of claim 16, wherein the drive mechanism is driven in a second direction opposite the first direction to pump fluid away from the surgical site.

18. A surgical instrument comprising:
a hub having a proximal portion and a distal portion that is configured to rotatably support a rotating member;
the rotating member extending through the hub, the rotating member having a proximal end and a distal end, the proximal end of the rotating member being configured to couple to an external driving mechanism; an impeller enclosure coupled to the distal portion of the hub and defining an impeller volume around an impeller; an impeller coupled to the distal end of the rotating member and configured to accelerate fluid flowing into or out of the impeller volume; and
an opening in the rotating member such that an interior of the hub is in fluid communication with the impeller volume.

19. The surgical instrument of claim 18, wherein the impeller enclosure defines an inlet and an outlet through which fluid enters and exits the impeller volume, respectively.

20. The surgical instrument of claim 18, wherein the impeller is a centrifugal impeller configured to accelerate fluid in a direction substantially perpendicular to an axis of rotation of the rotating member.

21. The surgical instrument of claim 1 further comprising a through hole in the proximal end of the rotating member for providing fluidic communication with the lumen during rotation of the driving mechanism.

22. The surgical instrument of claim 1 wherein the rotating member has an opening in an annular surface adjacent the sleeve for permitting fluidic communication with the impeller on an opposed side of the sleeve.

* * * * *